(12) United States Patent
Deslauriers et al.

(10) Patent No.: US 8,337,497 B2
(45) Date of Patent: Dec. 25, 2012

(54) METHODS FOR STERNAL CLOSURE (75) Inventors: Richard J. Deslauriers, Woodbury, CT (US); Eric Kolb, Sandy Hook, CT (US)

(73) Assignee: Doctors Research Group, Inc., Southbury, CT (US)

( * ) Notice: Subject to any disclaimer, the term of this patent is extended or adjusted under 35 U.S.C. 154(b) by 537 days.

(21) Appl. No.: 12/575,060

(22) Filed: Oct. 7, 2009

(65) Prior Publication Data
US 2011/0082498 A1  Apr. 7, 2011

(51) Int. Cl.
A61B 17/56 (2006.01)
A61B 17/58 (2006.01)
A61B 17/82 (2006.01)
A61F 2/30 (2006.01)

(52) U.S. Cl. .......................................... 606/74; 606/282
(58) Field of Classification Search .................. 606/280, 606/70, 71, 281, 282
See application file for complete search history.

(56) References Cited

U.S. PATENT DOCUMENTS

| | | |
|---|---|---|
| 3,030,951 A | 4/1962 | Mandarino |
| 3,112,743 A | 12/1963 | Cochran et al. |
| 3,802,438 A | 4/1974 | Wolvek |
| 3,945,376 A | 3/1976 | Kuehnegger |
| 4,201,215 A | 5/1980 | Crossett et al. |
| 4,279,248 A | 7/1981 | Gabbay |
| 4,458,365 A | 7/1984 | Wood |
| 4,512,346 A | 4/1985 | Lemole |
| 4,593,541 A | 6/1986 | Hollis |
| 4,730,615 A | 3/1988 | Sutherland et al. |
| 4,735,206 A | 4/1988 | Hewson |
| 4,813,416 A | 3/1989 | Pollak et al. |
| 4,944,753 A * | 7/1990 | Burgess et al. .............. 606/86 R |
| 5,163,598 A | 11/1992 | Peters et al. |
| 5,356,417 A | 10/1994 | Golds |
| 5,417,698 A | 5/1995 | Green et al. |
| 5,462,542 A | 10/1995 | Alesi, Jr. |

(Continued)

FOREIGN PATENT DOCUMENTS
WO  2006/060911 A1  6/2006

OTHER PUBLICATIONS

A Search Report and Written Opinion from corresponding International Appln. No. PCT/US2011/043502 dated Mar. 14, 2012 (11 pages).

(Continued)

Primary Examiner — Andrew Yang
(74) Attorney, Agent, or Firm — McCormick, Paulding & Huber LLP (57) ABSTRACT

A method for sternal closure of a separated sternum includes applying an adhesive to a portion of an incision between at least a first sternum portion and at least a second sternum portion and maintaining the first sternum portion proximate to the second sternum portion until the adhesive has bonded with the first sternum portion and the second sternum portion. The adhesive may be applied over substantially the entire length of the incision or may be applied in intervals. The method for sternal closure may also include compressing the first sternum portion and the second sternum portion together using one or more compression devices and introducing adhesive to contact regions where the compressive devices contact the sternum. The method may also include cutting an interface feature in the first and second sternum portions or spanning the incision between the first and second interface portions with a structural support.

32 Claims, 10 Drawing Sheets

U.S. PATENT DOCUMENTS

| | | |
|---|---|---|
| 5,514,137 A | 5/1996 | Coutts |
| 5,626,618 A | 5/1997 | Ward et al. |
| 6,007,538 A | 12/1999 | Levin |
| 6,051,007 A | 4/2000 | Hogendijk et al. |
| 6,358,270 B1 | 3/2002 | Lemer |
| 6,368,342 B1 | 4/2002 | Lemer |
| 6,540,769 B1 | 4/2003 | Miller, III |
| 6,712,821 B2 * | 3/2004 | Gabbay .................... 606/71 |
| 6,858,016 B2 | 2/2005 | Davaris et al. |
| 6,969,398 B2 | 11/2005 | Stevens et al. |
| 7,011,628 B2 | 3/2006 | LiDonnici |
| 7,252,841 B2 | 8/2007 | Constantz et al. |
| 7,361,179 B2 | 4/2008 | Rousseau et al. |
| 7,482,504 B2 * | 1/2009 | Brothers .................... 602/54 |
| 2005/0220771 A1 | 10/2005 | Deslauriers et al. |
| 2007/0218144 A1 * | 9/2007 | Lally .................... 424/601 |
| 2010/0179600 A1 | 7/2010 | Steger et al. |

OTHER PUBLICATIONS

Robert Selthofer et al., "Morphometric Analysis of the Sternum" as published in Coll. Antropol. 30 (2006) 1:43-47.

A.R. Casha et al., "A Biomechanical Study of Median Sternotomy Closure Techniques" as published in European Journal of Cardio-thoracic Surgery 15 (1999), pp. 365-369.

\* cited by examiner

METHODS FOR STERNAL CLOSURE

FIELD OF THE INVENTION

The present invention relates to surgical procedures and, more particularly, to sternal surgical procedures.

BACKGROUND OF THE INVENTION

During surgical procedures, an incision is made to provide a surgeon with access to a patient's internal organs. At the end of the surgical procedure, the incision is closed to the external environment, thereby allowing the patient to heal and recover from the surgery. For surgical procedures to organs within a patient's thoracic cage, such as the heart and lungs, the patient's sternum may need to be separated to provide the surgeon with access to the organs.

The sternum is an elongated, generally flat, bone located longitudinally in the center of the thorax. The sternum has a composite bone structure with a dense outer shell formed from cortical bone surrounding a low density core formed from cancellous bone. The sides of the sternum are connected to rib bones through cartilage to form the anterior section of the thoracic cage, which protects the lungs, heart and other organs from physical trauma.

A sternotomy is a surgical procedure in which a midline longitudinal incision is made through at least a portion of the sternum to allow the opposing portions to be separated to provide access to organs within the thoracic cage. The sternotomy may be median, whereby the midline incision is made over the entire longitudinal length of the sternum. Alternatively, the sternotomy may be a less invasive partial sternotomy or hemi sternotomy, whereby the midline longitudinal incision is made over only a portion of the length of the sternum along with one or more transverse incisions from a peripheral edge of the sternum to the midline incision, which allow a relatively small portion of the sternum to be separated. When the surgical procedure is complete, the separated opposing portions of the sternum are approximated to one another to close the incision and secured to one another so that the incision may heal.

Conventional closure devices for approximating and closing sternal incisions include wires, cables or bands that generally wrap around the sternum between the ribs to provide a compressive load across the sternal incision. While these conventional devices restrain the sternum portions from pulling apart, they do little to resist other forms of relative motion, for example, sliding of one cut surface relative to the other or flexing motion about the incision. These non-prevented relative movements may result in pain and discomfort for the patient, as well as more severe complication such as infections. Additionally, the relative movement may cause soft fibrous scar tissue to form across the incision, rather than the desired bone growth. The fibrous scar tissue must be subsequently removed with further surgical procedures.

Relative motion between the two sternal portions may also cause the conventional devices to loosen. For example, in the case of devices secured by twisted wire, the wire may untwist. More severely, the relative motion may cause the conventional devices to cut into and pull through the sternum bone, which also results in a loosening of the devices and separation of the sternal portions. This separation may delay healing or may result in additional surgical procedures to tighten or replace the conventional closure devices. The loosening or pulling through of the conventional devices may be caused by loading that the patient cannot practically control, such as cyclic loading due to normal respiration as well as less frequent high cycle loads generated during coughing or sneezing.

Another conventional closure device includes a metal plate that is fastened to an anterior surface of the sternum. While the metal plate inhibits relative movement between the two sternal portions better than conventional wires and cables, the metal plate has its own limitations and disadvantages. For instance, the thickness of metal plate closure devices results in discomfort to the patient. Additionally, the relative movement between the sternal portions may result in a failed screw purchase. With a failed screw purchase, one or more of the screws fastening the metal plate to the sternum strips the sternum bone, allowing the screw or screws to pull out of the bone. The loose screw or screws allow the metal plate to loosen from the sternum causing pain and discomfort for the patient. Furthermore, metal plate closure devices are costly and difficult, to remove in the event there is a need for future access to the thoracic cavity.

Accordingly, there is a need for an improved method for sternal closure that overcomes the deficiencies of the prior art.

SUMMARY OF THE INVENTION

According to the present invention, a method for sternal closure includes applying an adhesive to a portion of an incision between at least a first sternum portion and at least a second sternum portion and maintaining the first sternum portion proximate to the second sternum portion until the adhesive has bonded with the first sternum portion and the second sternum portion. The adhesive is formed from a biocompatible polymeric material that is preferably osteoconductive. The adhesive resists relative movement between the first sternum portion and the second sternum portion once bonded.

According to the present invention, the adhesive may be applied over substantially the entire length of the incision or may be applied in intervals with gaps in between to promote natural bone growth.

According to one embodiment of the present invention, the method for sternal closure also includes compressing the first sternum portion and the second sternum portion together. Compression may be provided by compressive devices that are either temporary or permanent. For example, temporary compressive devices may include clamps that are removed once the adhesive cures. Permanent compressive devices may include wires, cables and bands that pass around the sternum to hold the first and second sternum portions together. Additionally, adhesive may be introduced to contact regions where the compressive devices are in contact with, or will be in contact with, the first and second sternum portions to enhance strength and rigidity.

The methods according to the present invention may also include cutting at least one interface feature in the first sternum portion and the second sternum portion to enhance the bond between the portions. The interface feature may enhance the adhesive bond provided by the adhesive or may be used to provide a mechanical joint between the first and second sternum portions. The bond between the first and second sternum portions may also be enhanced by providing a structural support spanning the incision between the first sternum portion and the second sternum portion.

These and other objects, features and advantages of the present invention will become apparent in light of the following detailed description of non-limiting embodiments, with reference to the accompanying drawings.

DETAILED DESCRIPTION OF A PREFERRED EMBODIMENT

Figure 1:
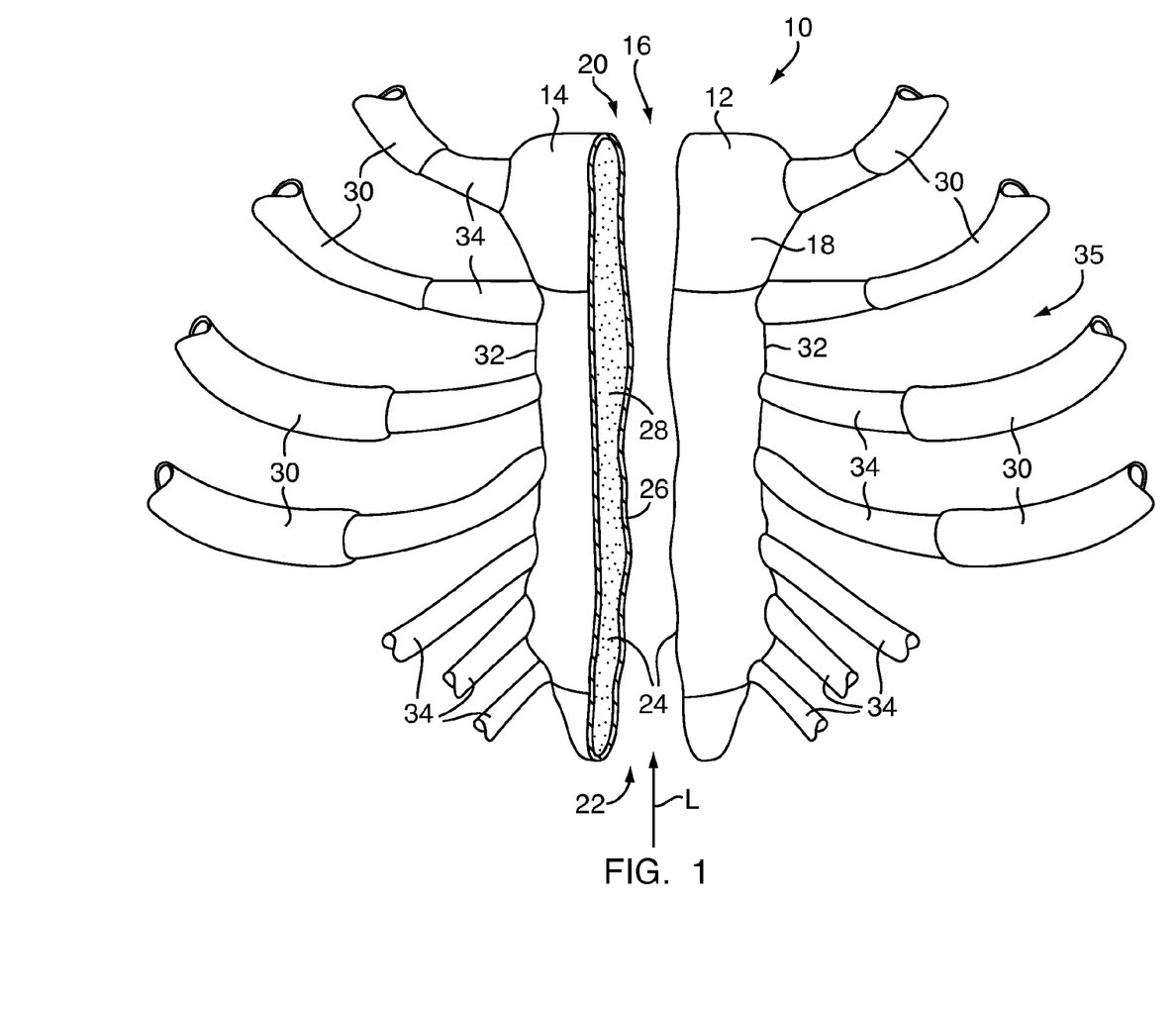
FIG. 1 is a perspective view of a separated sternum.

Referring to FIG. 1, the present invention provides a method for closure of a sternum 10 that has been separated into a first sternum portion 12 and a second sternum portion 14 by an incision 16, for example, from a surgical procedure such as a median sternotomy. The incision 16 extends in a longitudinal direction L approximately along a midline of the anterior surface 18 of the sternum 10 from an upper end 20 to a lower end 22. The incision 16 forms a cut surface 24 on each of the first and second sternum portions 12 and 14, exposing the sternum's composite bone structure having a shell of cortical bone 26 surrounding a core of cancellous bone 28. A plurality of rib bones 30, shown in FIG. 2, are connected to peripheral edges 32 of the sternum 10 by cartilage 34 to form a thoracic cage 35, shown in FIG. 2, for protecting internal organs from physical trauma.

Figure 2:
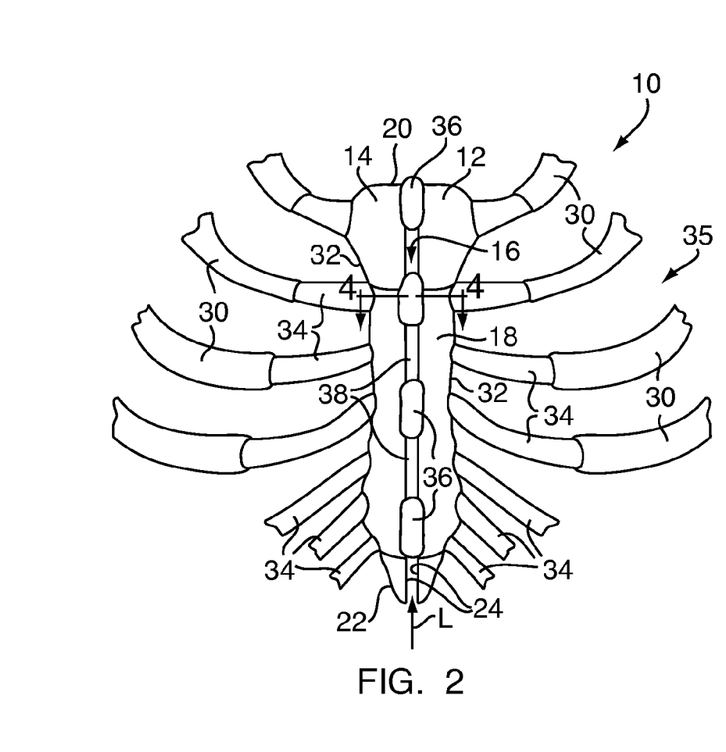
FIG. 2 is a front view of the separated sternum of FIG. 1 with adhesive placed therein in accordance with an embodiment of the present invention.

Referring to FIG. 2, at the end of the surgical procedure, such as a sternotomy, an adhesive 36 is applied to the at least one of the first and second sternum portions 12 and 14 and the first and second sternum portions 12 and 14 are brought proximate to one another. Preferably, the adhesive 36 is applied as a liquid or taffy-like material, as will be discussed in more detail below. When the sternum portions 12 and 14 are brought together, the adhesive 36 on one sternum portion, for example, the first sternum portion 12, contacts the opposing cut surface 24 of, for example, the second sternum portion 14. Thus, the incision 16 between the first and second sternum portions 12 and 14 becomes partially filled with the adhesive 36. The adhesive 36 is applied so that it is located at a plurality of longitudinal locations along the incision 16 interrupted by gaps 38 between each instance of adhesive 36. Preferably, the adhesive 36 covers approximately twenty percent (20%) to approximately eighty percent (80%) of the longitudinal length of the incision 16 and, even more preferably, covers approximately thirty percent (30%) to approximately seventy percent (70%) of the longitudinal length of the incision 16.

Figure 3:
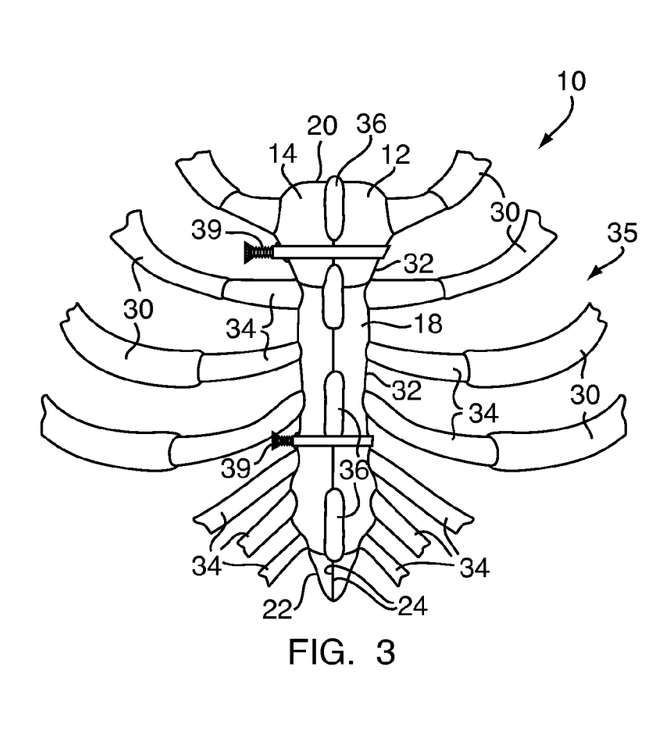
FIG. 3 is a front view of the separated sternum of FIG. 2 with first and second sternum portions compressed.

Once the adhesive 36 has been applied to the sternum 10 within incision 16, the first and second sternum portions 12 and 14 may be maintained proximate to one another until the adhesive 36 has bonded with each of the first and second sternum portions 12 and 14. More preferably, as seen in FIG. 3, the first and second sternum portions 12 and 14 are compressed together, with the cut surfaces 24 abutting one another. The first and second sternum portions 12 and 14 may be permanently compressed, as will be discussed in more detail below, or the first and second sternum portions 12 and 14 may be temporarily compressed through the use of clamps 39 or other known compressive devices. Compressing the first and second sternum portions 12 and 14 together forces some of the adhesive 36 into the porous structure of the internal cancellous bone 28, thereby increasing the bond formed when the adhesive polymerizes, as will be discussed in more detail below. The clamps 39 are then removed once the adhesive 36 has cured.

Figure 4:
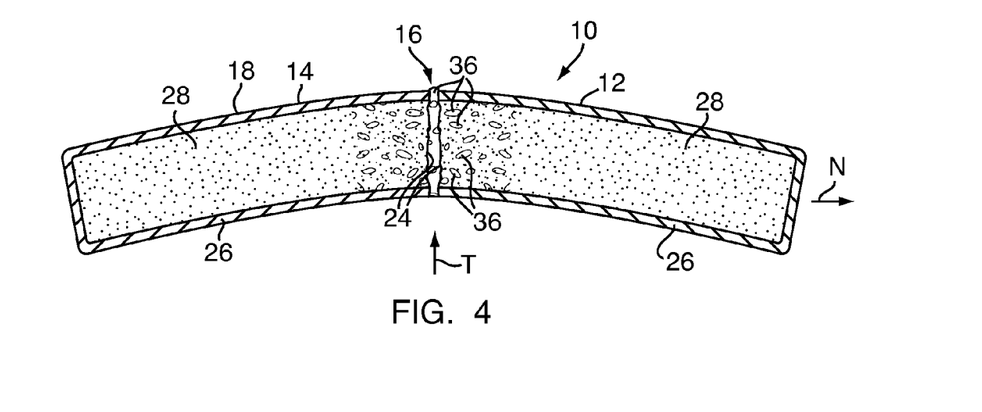
FIG. 4 is a cross-sectional view of the separated sternum with adhesive placed therein of FIG. 2.

Referring to FIG. 4, the adhesive 36 may be applied to the cut surfaces 24 within incision 16 over substantially the entire thickness of the sternum 10 to maximize contact with the sternum portions 12 and 14 and to provide a strong bond between the first and second sternum portions 12 and 14. Additionally, applying the adhesive 36 to substantially the entire thickness of the cut surface 24 allows the adhesive 36 to bond with both the cortical bone 26 and the cancellous bone 28 of the first and second sternum portions 12 and 14.

The bond formed by adhesive 36 between the first and second sternum portions 12 and 14 is preferably both chemical, due to adhesive properties of the adhesive 36, and mechanical, due to a portion of the adhesive 36 partially invading or infiltrating the porous structure of the cancellous bone 28 and/or cortical bone 26 of the sternum 10. Additionally, the adhesive 36 preferably has expansion characteristics that facilitate the bonding of the adhesive 36 to the first and second sternum portions 12 and 14. For example, once the adhesive 36 has been applied to the first and second sternum portions 12 and 14 and the portions have been brought proximate to one another, the adhesive 36 may expand into the porous structure of the cancellous bone 28. Once the first and second sternum portions 12 and 14 have been approximated, the cortical bone 26 acts as a seal to guide the expanding adhesive 36 into the cancellous bone 28. Preferably, the adhesive expands into the cancellous bone 28 of the first and second sternum portions 12 and 14 in the range of approximately 1 mm to approximately 10 mm. The adhesive 36 then polymerizes within the porous structure of the cancellous bone 28 to provide a strong mechanical bond between the first and second sternum portions 12 and 14.

The bonded adhesive 36 resists relative motion between the first and second sternum portions 12 and 14 and holds the incision 16 closed to allow bone growth between the first and second sternum portions 12 and 14 so that the patient may heal after the surgical procedure. In particular, the bonded adhesive 36 prevents the first and second sternum portions 12 and 14 from shearing with one another in the longitudinal direction L, shown in FIG. 2, from flexing about the incision 16 due to loads in the transverse direction T, shown in FIG. 4, and from separating in a normal direction N, normal to the cut surfaces 24, as shown in FIG. 4. Thus, the bond provided by adhesive 36 prevents shearing, flexing and separation of the first sternum portion 12 from the second sternum portion 14 due to loads from physical trauma as well as cyclical loads caused by breathing, sneezing, coughing or the like.

The adhesive 36 is preferably a biocompatible polymeric adhesive material, which is osteoconductive and promotes bone growth when used in medical procedures. Suitable biocompatible polymeric adhesive material for the present invention may be formed from a polyurethane/polyurea such as the KRYPTONITE™ bone matrix product, available from DOCTORS RESEARCH GROUP, INC. of Southbury, Conn., and also described in U.S. patent application Ser. No. 11/089,489, which is hereby incorporated by reference in its entirety.

The biocompatible polymeric material may combine an isocyanate with one or more polyols and/or polyamines, along with optional additives (e.g., water, filler materials, catalysts, surfactants, proteins, and the like), permitting the materials to react to form a composition that comprises biocompatible polyurethane/polyurea components. As referred to herein, the term "biocompatible polyurethane/polyurea components" includes, inter alia, biocompatible polyester urethanes, biocompatible polyether urethanes, biocompatible poly(urethane-ureas), biocompatible polyureas, and the like, and mixtures thereof.

Certain embodiments may comprise biocompatible polyurethane/polyurea components present in an amount in the range of from about twenty percent to about ninety percent (20% to about 90%) by weight of the composition, with the balance comprising additives. Certain embodiments of the compositions made according to the present invention may comprise biocompatible polyurethane/polyurea components present in an amount in the range of from about fifty percent to about eighty percent (50% to about 80%) by weight of the composition, with the balance comprising additives.

The biocompatible polymeric material is initially prepared in a liquid state, which is chemically adhesive. As the biocompatible polymeric material cures, it will pass through a taffy-like state, during which it is highly chemically adhesive. The biocompatible polymeric material then passes into a putty-like state in which the material's adhesive properties are reduced and the material is easily malleable and may be shaped and sculpted. The biocompatible polymeric material then cures into a final solid state. Since the adhesive properties of the biocompatible polymeric material are greatest when the material is in the liquid or taffy-like state, the material is preferably in either the liquid state or the taffy-like state when applied as adhesive 36. In the final solid state, the biocompatible polymeric material has a porous structure that promotes bone growth and is able to be cut in a similar manner to bone with a sternal saw. Thus, when used in sternal closure procedures according to the present invention, quick access to the thoracic cavity may be gained in the event that future surgical procedures are necessary.

Referring back to FIG. 2, as discussed above, in one embodiment, the adhesive 36 is applied intermittently along the incision 16 to provide the bond between the first and second sternum portions 12 and 14. The gaps 38 formed between the instances of adhesive 36 provide direct bone to bone contact between the first and second sternum portions 12 and 14, when compressed, which allows for direct bone growth between the first and second sternum portions 12 and 14 as the patient heals, thereby promoting natural healing after the surgical procedure. Preferably, the adhesive 36 has a porous structure and has osteoconductive properties so that bone growth also occurs between the first and second sternum portions 12 and 14 through the adhesive as the patient heals. The combination of the adhesive's mechanical strength, adhesiveness and porous structure makes the adhesive 36 unique in its utility as a sternal closure material.

For example, the peak load across the incision 16 of the sternum 10 due to coughing is approximately 1500 N as taught by the article entitled "A Biomechanical Study of Median Sternotomy Closure Techniques" by A. R. Casha et al. as published in the European Journal of Cardio-thoracic Surgery 15 (1999) 365-369, which is hereby incorporated by reference in its entirety. The load that the adhesive 36 is capable of supporting can be calculated using the equation:

$$LOAD = S \times A,$$

where,

S is the strength of the material used for the adhesive 36; and

A is the surface area of the cut surface 24 coated with adhesive 36.

The KRYPTONITE™ bone matrix product, which is suitable as the adhesive 36 as discussed above, has a fatigue strength of approximately 2 MPa (as tested per ASTM F2118). The surface area of each cut surface 24 will vary patient to patient, but there average cross sectional area is approximately 14.5 cm(2) women and approximately 17.0 cm(2) for men, as calculated from data provided in the article entitled "Morphometric Analysis of the Sternum" by Robert Selthofer et al. as published in Coll. Antropol. 30 (2006) 1: 43-47, which is hereby incorporated by reference in its entirety. Thus, the load that the KRYPTONITE™ bone matrix product can support if the entire cut surface 24 is coated can be approximately 2900 N for women and approximately 3500 N for men, which is over two times the approximate peak load of 1500 N. Therefore, applying the adhesive 36 to approximately half of the cut surfaces 24 in intervals, as discussed above, will provide sufficient strength to bond the first and second sternum portions 12 and 14 together, while allowing the other half of the cut surfaces 24 to contact each other to facilitate bone growth. As should be understood by those skilled in the art, there may be a large variation in the peak load value and the surface area of the cut surfaces 24 depending upon the patient's age, size, fitness and various other factors.

Although described as applying the adhesive 36 prior to approximating the first and second sternum portions 12 and 14, the method for sternal closure may instead apply the adhesive 36 to one or both of the cut surfaces 24 within the incision 16 after bringing the first and second sternum portions 12 and 14 proximate to one another.

Preferably, the cut surfaces 24 are prepared for the adhesive 36 prior to application of the adhesive 36 to remove surface contaminants that may affect adhesion and/or to expose the bone porosity to improve the mechanical bond provided by the adhesive 36. Preferably, no bone wax or other hemostatic material is used during the sternal procedure. If bone wax or another hemostatic material is not used, the cut surfaces 24 may be treated to remove, bone fragments, fat, blood, fluids, soft tissues or any other material that could affect adhesion between the cut surfaces 24. However, if bone wax or other hemostatic materials are used, they are also preferably removed prior to placement of the adhesive 36, along with any other material that could prevent bone growth. For example, simple mechanical cleaning, using a suitable brush or the like, or the use of carbon dioxide or other gases or liquids may be used to prepare the cut surfaces 24. If using commercially available lavage systems, an appropriate nozzle may be employed to protect the organs under the sternum 10 while preparing and drying the cut surfaces 24. Even more preferably, the lavage system may use a nozzle designed to prepare the cut surface 24 and to apply the adhesive 36 at substantially the same time.

Figure 5:
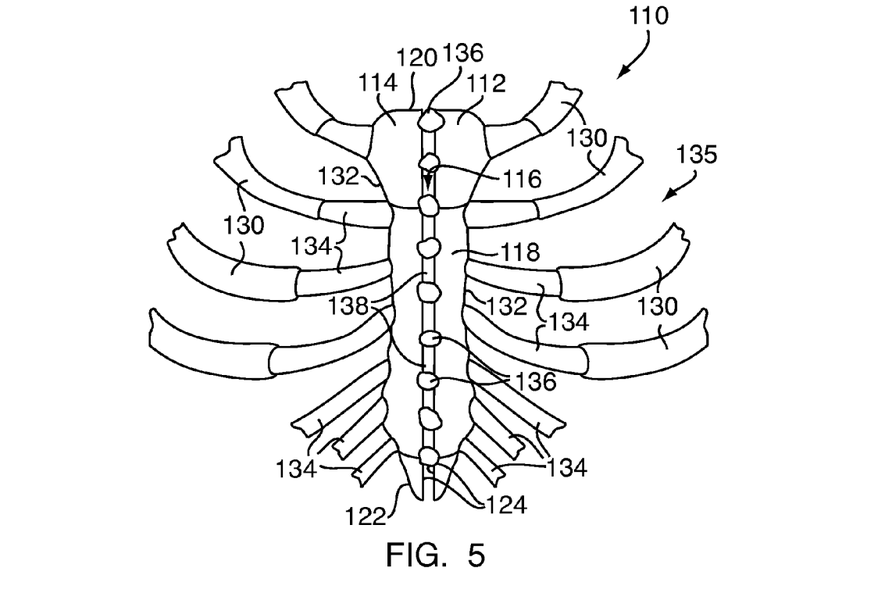
FIG. 5 is a front view of the separated sternum of FIG. 1 with adhesive placed therein in accordance with another embodiment of the present invention.

Referring to FIG. 5, wherein like numerals represent like elements, both the size and frequency of application of adhesive 136 along the longitudinal incision 116 may be varied to alter the bond strength between the first and second sternum portions 112 and 114. Additionally, the size and/or frequency of application of adhesive 136 may be changed to increase the size and frequency of gaps 138, thereby providing more bone to bone contact between the first and second sternum portions 112 and 114 to promote additional natural bone growth, when the first and second sternum portions 112 and 114 are compressed together as discussed above in connection with FIG. 3.

Figure 6:
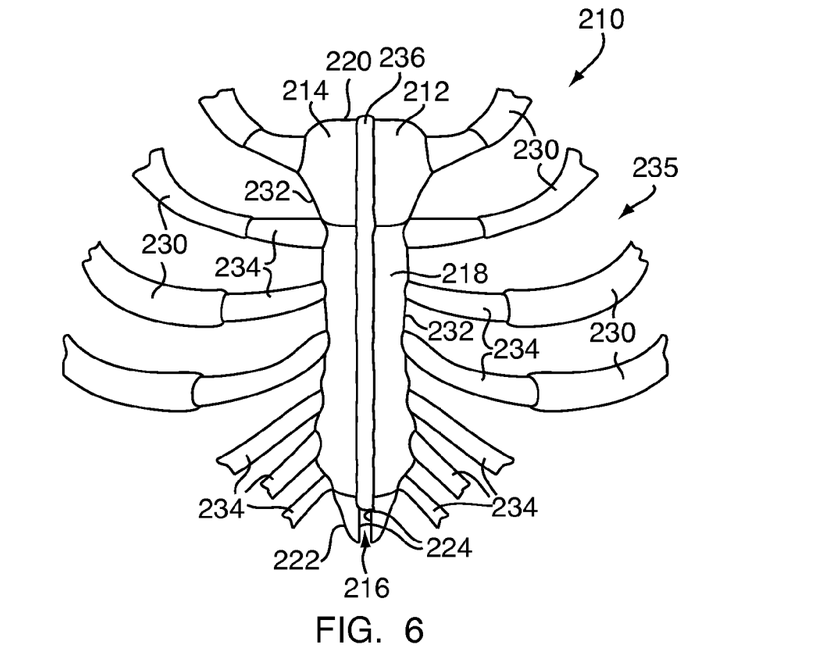
FIG. 6 is a front view of the separated sternum of FIG. 1 with adhesive placed therein in accordance with another embodiment of the present invention.

Referring to FIG. 6, in another embodiment of the present invention, the adhesive 236 may be applied over substantially the entire length of the incision 216 to increase the strength of the bond between the first and second sternum portions 212 and 214. In this embodiment, it would be particularly advantageous for the adhesive 236 to have osteoconductive properties so that bone growth between the first and second sternum portions 212 and 214 occurs through the adhesive 236, thereby allowing the patient to heal.

Figure 7:
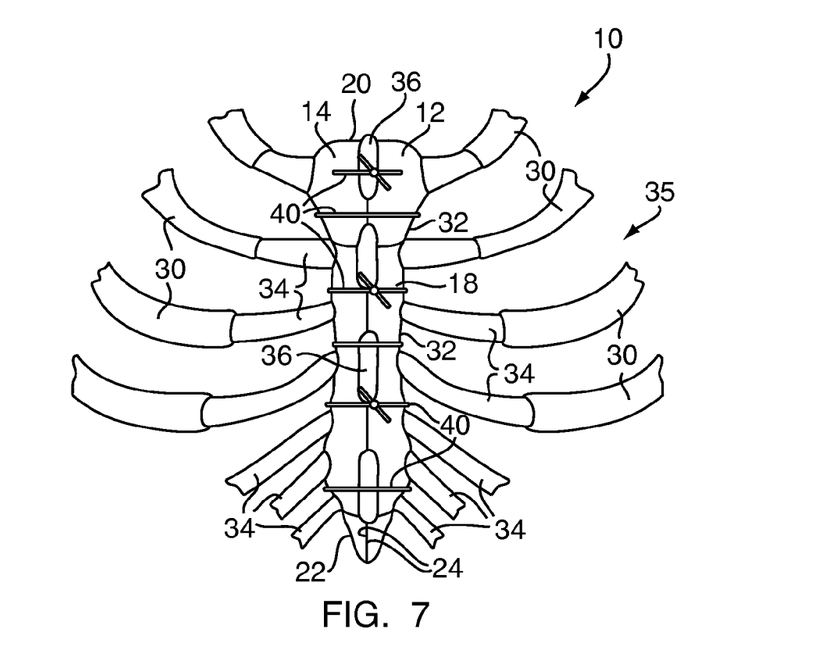
FIG. 7 is a front view of the separated sternum with adhesive placed therein of FIG. 2 with an additional compression device.

Referring to FIG. 7, the method for sternum closure of the present invention may also include securing the first and second sternum portions 12 and 14 together with compressive devices 40 that are permanent, such as wires, cables, bands or straps that pass around the sternum to hold the first and second sternum portions 12 and 14 together. The compressive devices 40 may be positioned around the sternum 10 while the adhesive 36 is in the liquid or taffy-like state to maintain the position of the first and second sternum portions 12 and 14 proximate to one another while the adhesive 36 cures to form the adhesive bond discussed above. In this embodiment, the compressive devices 40 provide the compressive force for securing the first sternum portion 12 and the second sternum portion 14 together during the healing process, thereby ensuring that the sternum portions 12 and 14 do not separate. The adhesive bond formed by adhesive 36 inhibits flexing and shearing motion of the first and second sternum portions 12 and 14 relative to one another, which would still be possible if the first and second sternum portions 12 and 14 were secured by only compressive devices 40. Inhibiting relative movement between the first and second sternum portions 12 and 14 with the adhesive 36 may also reduce the degree to which the compressive devices 40 cut into the sternum 10, preventing loosening of the compressive devices 40, separation of the closed sternum 10 and potential discomfort to the patient.

Additionally, by using the adhesive 36 with the compressive devices 40, relatively fewer compressive devices 40 may be used to secure the sternum portions, when compared to conventional sternal closure devices. For example, in addition to the adhesive 36, the present invention may use only two compressive devices 40, one at either end of the sternum 10, to provide adequate stability to the closed sternum 10. Reducing the number of compressive devices 40, such as wires, may decrease the risk of injury to the patient, because fewer wires or cables must be passed behind the sternum 10 and across surgical grafts both during the initial procedure and during revision surgery, if necessary.

Figure 8:
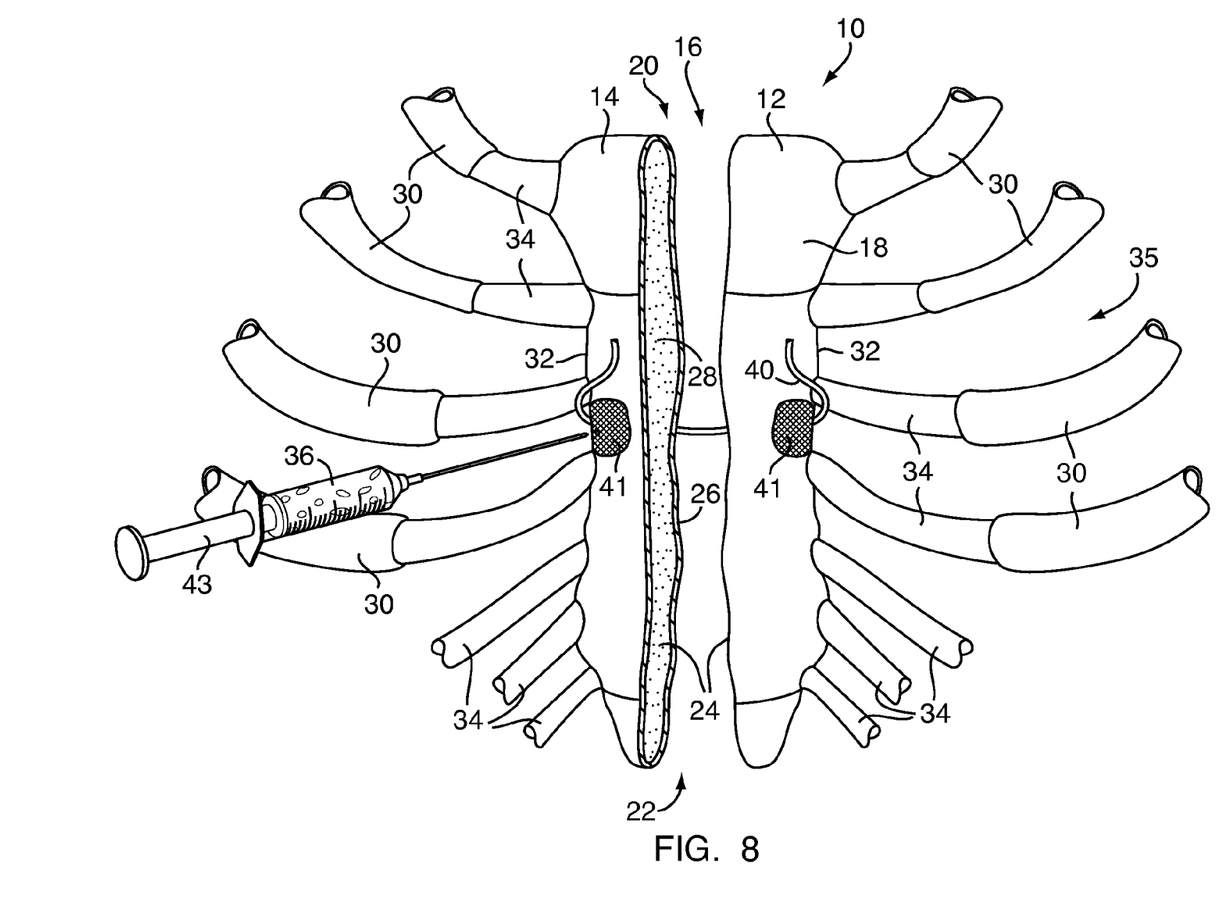
FIG. 8 is a perspective view of another embodiment of the separated sternum with adhesive placed therein of FIG. 7.

Referring to FIG. 8, adhesive 36 may also be injected into or through the outer cortical bone 26 of the sternum 10 in contact regions 41 where the compressive devices 40 are in contact with, or will be in contact with, the first and second sternum portions 12 and 14 after the sternum 10 has been closed. For example, the adhesive 36 may be injected with delivery means 43, such as a syringe, into the sternum 10 through the cortical bone 26 at the anterior surface 18 along the peripheral edges 32 of the sternum 10 between rib bones 30. Alternatively, the adhesive 36 may be delivered to the contact region 41 by injection through the cancellous bone 28 at the cut surface 24. The adhesive 36 occupies space within the porous structure of the cancellous bone 28 and/or cortical bone 26, where it cures to add strength and stiffness to the cancellous bone 28 and/or cortical bone 26 in the contact regions 41. The injected adhesive 36 makes it more difficult for the compressive devices 40 to cut into the bone, thereby preventing loosening of the compressive devices 40 and/or pain experienced by the patient. The application of adhesive 36 to the contact regions 41 may be particularly beneficial for patients with weak osteoporotic bones.

Figure 9:
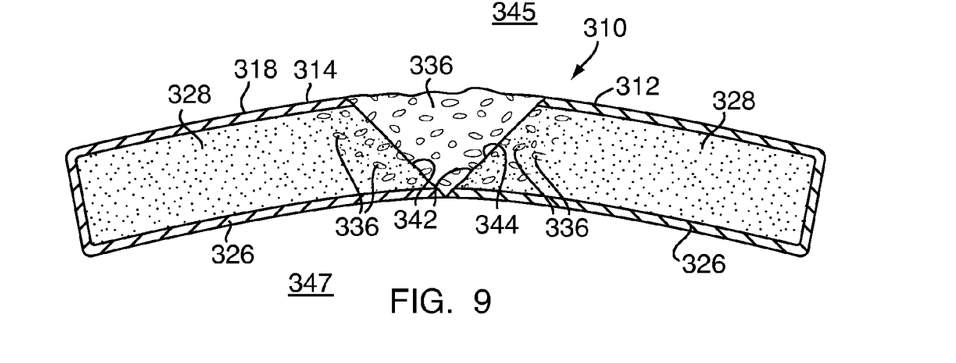
FIG. 9 is a cross-sectional view of another embodiment of the separated sternum with adhesive placed therein of FIG. 2.

Referring to FIG. 9, the method for sternal closure according to another embodiment of the present invention may also include forming interface features 341 in the first and second sternal portions 312 and 314 to facilitate healing and/or increase strength of the bond between the first and second sternum portions 312 and 314. For instance, the cut surfaces 24, shown in FIG. 4, may be formed into chamfers 342, each sloping inward toward the opposing first or second sternum portion 312 or 314. The chamfers 342 may extend over substantially the entire longitudinal length of the sternum 310 or may be located only at intermittent locations, i.e. only where adhesive 336 is to be applied, for example, as shown in the embodiment of FIG. 2.

When the first and second sternum portions 312 and 314 are brought proximate to one another during the sternum closure procedure, the chamfers 342 form a cavity 344, open to and accessible from an anterior 345 of the sternum 310. The cavity 344 may be filled with the adhesive 336 during the adhesive application process. Since the cavity 344 is highly accessible, it makes the process of applying the adhesive 336 easier for practitioners. The chamfers 342 also have an increased surface area with which to bond to the adhesive 336 when compared to the cut surfaces 24, shown in FIG. 4, thereby providing increased strength in the bond formed between the first and second sternum portions 312 and 314. Additionally, any expansion of the adhesive 336 during the curing process is likely to occur outward from the cavity 344 of the sternum 310, rather than into an interior 347 of the thoracic cage (not shown) of the patient, where it could potentially cause damage.

Although shown as chamfers 342, one skilled in the art should understand that the interface features 341 may take other forms that provide an improved interface to facilitate healing and/or increase strength, for example, flanges may be formed in the first and second sternal portions 312 and 314.

Figure 10:
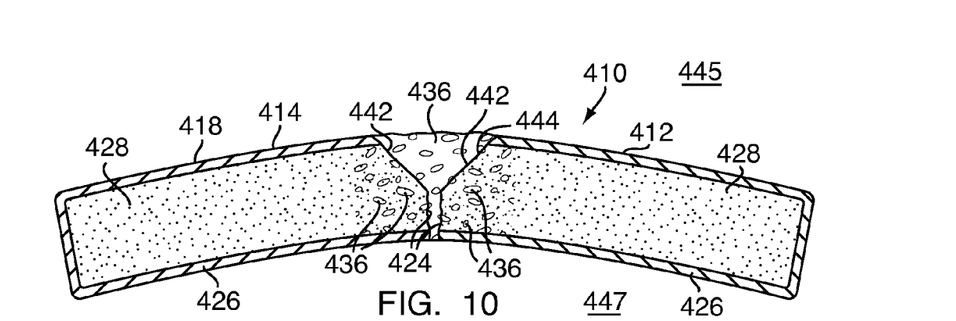
FIG. 10 is a cross-sectional view of another embodiment of the separated sternum with adhesive placed therein of FIG. 2.

Referring to FIG. 10, in another embodiment of the present invention, the cut surfaces 424 of the first and second sternum portions 412 and 414 may be formed with only partial chamfers 442 at the anterior surface 418, with the inner cut surfaces 424 remaining. The chamfers 442 may extend over substantially the entire longitudinal length of the sternum 410 or may be located only at intermittent locations, i.e. only where adhesive 436 is to be applied, for example, as shown in the embodiment of FIG. 2.

When the first and second sternum portions 412 and 414 are brought proximate to one another, during the sternum closure procedure, the cut surfaces 424 contact one another and the chamfers 442 form the cavity 444, open to and accessible from the anterior 445 of the sternum 410. Since the chamfers 442 extend over only a portion of the cut surfaces 424, the cavity 444 is smaller than the cavity 344, shown in FIG. 9. The cavity 444 may be filled with the adhesive 436 as discussed above to form the bond between the first and second sternum portions 412 and 414. The cut surfaces 424 contact one another, thereby allowing for direct bone growth between the first sternum portion 412 and the second sternum portion 414 to promote natural healing after the surgical procedure. Additionally, as discussed in connection with FIG. 8, any expansion of the adhesive 436 during the curing process is likely to occur outward from the cavity 444 of the sternum 410, rather than into the interior 447 of the thoracic cage (not shown) of the patient, where it could potentially cause damage.

Figure 11:
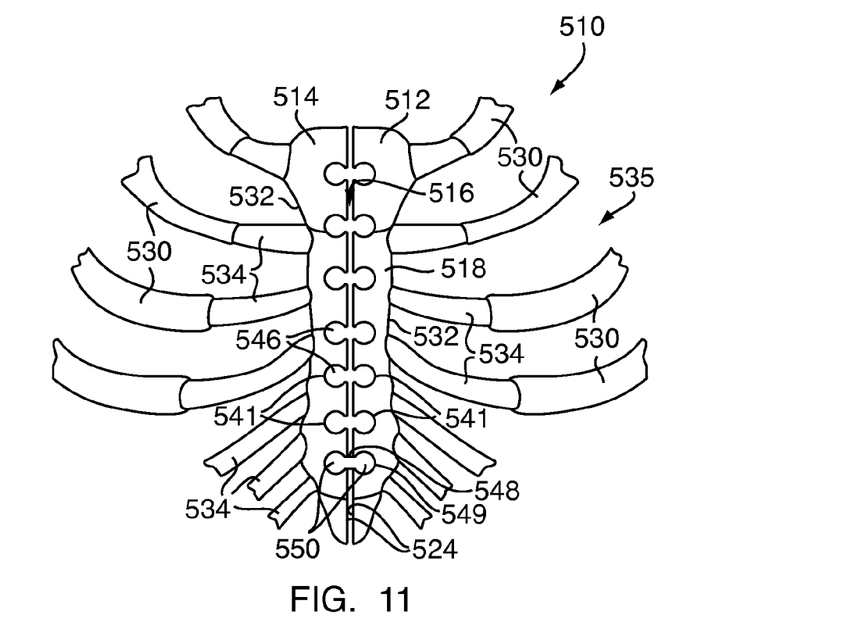
FIG. 11 is a front view of the separated sternum of FIG. 1 with a mechanical joint formed therein in accordance with another embodiment of the present invention.

Referring to FIG. 11, the method for sternal closure according to the present invention may also include inserting a structural member 549 into the interface feature 541 to span the incision 516 between the first and second sternum portions 512 and 514. For instance, interface features 541 may be formed as geometric features 546 for accommodating structural members such as polymeric inserts 548 to provide mechanical joints between the first and second sternum portions 512 and 514. The geometric features 546 may be formed to be circular, as shown, or may be formed in various other shapes capable of retaining at least a portion of the polymeric insert 548. The geometric features 546 are formed through the anterior surface 518 of the first and second sternum portions 512 and 514, penetrating the cut surfaces 524 of the first and second sternum portions 512 and 514. The geometric features 546 may extend entirely or, more preferably, only partially through the thickness of the sternum 510. Additionally, the geometric features 546 are preferably formed to be substantially opposite one another on opposing first and second sternum portions 512 and 514 to ease insertion of the polymeric insert 548.

The polymeric insert 548 is formed with end locks 550 which correspond to the shape of geometric features 546, for example, if the geometric features 546 are round, the polymeric insert 548 may be provided with round end locks 550. Similarly, if the geometric features 546 are formed in a triangular shape, the polymeric insert 548 may be formed in a bowtie shape with end locks 550 to be accommodated within the geometric features 546. Preferably, the polymeric inserts 548 are formed from a material that has osteoconductive properties to promote bone growth as the sternum 510 heals after closure. Even more preferably, the polymeric inserts 548 are formed from substantially the same material as the adhesive 36, shown in FIG. 2.

During the sternal closure procedure, the practitioner forms the geometric features 546 in the first and second sternum portions 512 and 514. Preferably, an instrument or system is used by the practitioner to precisely form the geometric features 546 to the appropriate size, shape and depth. Once the geometric features 546 have been formed, the end locks 550 of each polymeric insert 548 are accommodated within opposing geometric features 546. Adhesive 536 may be applied to the surface of the polymeric insert 548 to secure it within the geometric feature 546. The mechanical joint formed by accommodating the polymeric insert 548 within the geometric feature 546 prevents separation of the first and second sternum portions 512 and 514.

Figure 12:
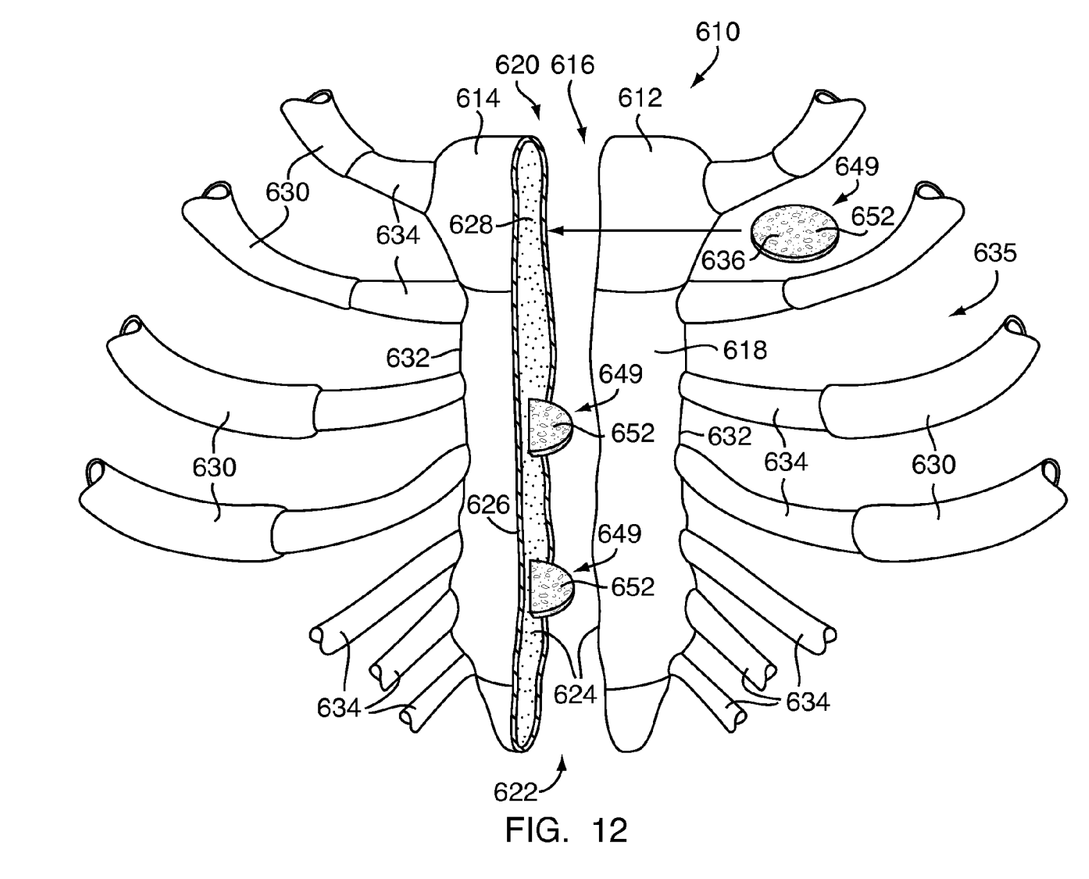
FIG. 12 is a perspective of the separated sternum of FIG. 1 with structural member placed therein in accordance with another embodiment of the present invention.

Referring to FIG. 12, in another embodiment of the present invention, the structural members 649 spanning the incision 616 may include one or more polymeric biscuits 652. The polymeric biscuits 652 may be pressed into the cancellous bone 628 of sternum 610 to add support after closure. Preferably, the biscuits 652 are formed from a material that has osteoconductive properties to promote bone growth as the sternum 610 heals, and, even more preferably, the biscuits 652 are formed from substantially the same material as the adhesive 36, shown in FIG. 2.

During the sternal closure procedure, the biscuits 652 are partially pressed into the cancellous bone 628 of one of the sternum portions, for example, the second sternum portion 614. Preferably, the biscuits are pressed into the cancellous bone 628 so that approximately half of the biscuit is accommodated within the second sternum portion 614. The adhesive (not shown) may then be applied to the cut surfaces 624. The first and second sternum portions 612 and 614 may then be brought proximate to one another. As the first and second sternum portions 612 and 614 are brought proximate to one another, the biscuits 652 are pressed into the cancellous bone 628 of the other sternum portion, for example, the first sternum portion 612. Once the sternum 610 has been closed, the biscuits 652 provide structural support to the sternum 610 by spanning the incision 616. Additionally, adhesive (not shown) may be applied around the biscuit 652, prior to pressing the biscuit into the cancellous bone 628, to provide adhesive strength to the closed incision 616. The application of adhesive (not shown) around the biscuit 652 may be in addition to or instead of the application of adhesive (not shown) to the cut surfaces 624.

Figure 13:
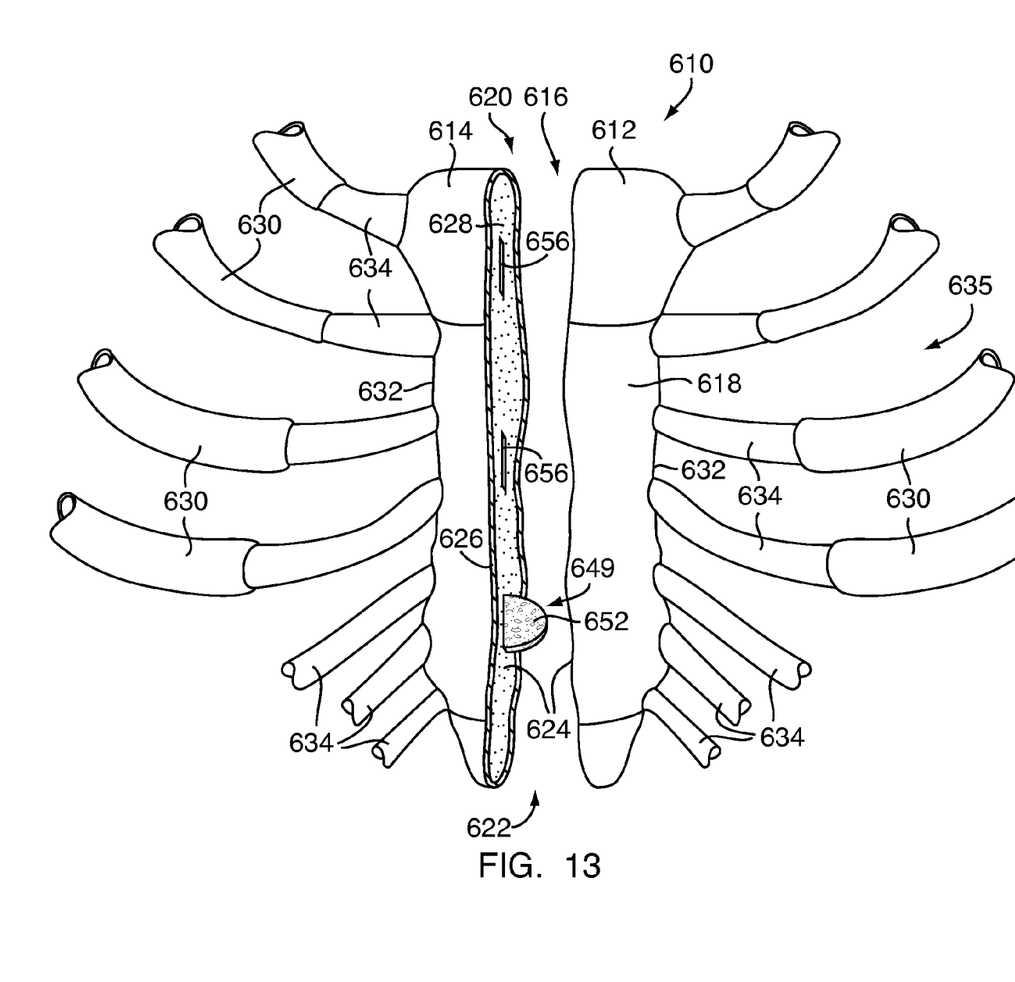
FIG. 13 is a perspective of another embodiment for accommodating the structural member within the separated sternum of FIG. 12.

Referring to FIG. 13, rather than pressing the biscuits 652 into the cancellous bone 628, spacer accommodations 656 may be formed by cutting away portions of the cancellous bone 628 while the first and second sternum portions 612 and 614 are separated. The biscuits 652 may be coated with adhesive (not shown), if desired, and inserted into the spacer accommodations 656 of either the first sternum portion 612 or the second sternum portion 614. The remainder of each biscuit 652 is then inserted into the other of the first sternum portion 612 or the second sternum portion 614 when the first and second sternum portions 612 and 614 are brought proximate to one another. This embodiment may be particularly beneficial for patients with relatively rigid cancellous bone 628, where pressing the biscuit 652 into the cancellous bone 628 is impractical.

Figure 14:
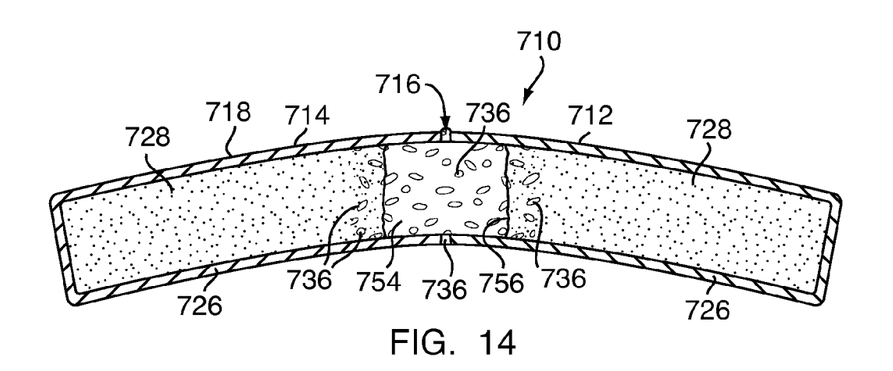
FIG. 14 is a cross-sectional view of another embodiment of the separated sternum with the structural member placed therein of FIG. 12.

Referring to FIG. 14, in another embodiment of the present invention, a putty-like material volume 754 may be inserted into spacer accommodations 756 of the first and second sternum portions 712 and 714, after which the putty-like material volume 754 cures to form the structural spacer spanning the incision 716. Preferably, the putty-like material volume 754 is formed from an osteoconductive material, and, even more preferably, from the same material as the adhesive 736. The space accommodations 756 are formed by cutting away portions of cancellous bone 728 while the first and second sternum portions 712 and 714 are separated. After the portions of cancellous bone 728 have been cut away from each of the first and second sternum portions 712 and 714 to form the spacer accommodations 756, the putty-like material volume 754 can then be shaped, if necessary, and inserted into the spacer accommodation 756 of either the first sternum portion 712 or the second sternum portion 714. The remainder of the putty-like material volume 754 is then inserted into the other of the first sternum portion 712 or the second sternum portion 714 when the first and second sternum portions 712 and 714 are brought proximate to one another. The putty-like material volume 754 then cures within the spacer accommodations 756 to add structural support to the closed sternum 710 by spanning the incision 716.

Figure 15:
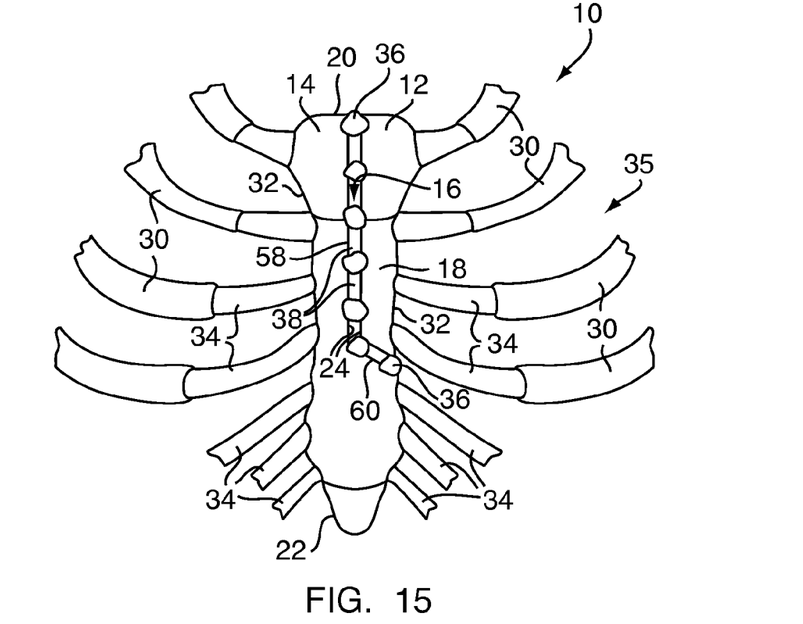
FIG. 15 is a front view of a sternum closed by adhesive after a partial sternotomy according to another embodiment of the present invention.

Although the methods for sternal closure of the present invention have thus far been described with regard to a median sternotomy, it should be understood by those skilled in the art that the present invention may also be used for other surgical procedures. For example, referring to FIG. 15, the methods according to the present invention may also close a sternum 10 after a partial sternotomy wherein the incision 16 includes a longitudinal portion 58 extending from the upper end 20 or lower end 22 of the sternum partway along the midline of the anterior surface 18 to a transverse incision portion 60, which extends to the peripheral edge 32, to separate the sternum 10 into first and second sternum portions 12 and 14. During the sternum closure procedure, adhesive 36 may be applied to the incision 16 in the same manner discussed above. Additionally, the adhesive 36 is preferably applied to both the transverse portion 60 and the longitudinal portion 58 of the incision 16 to provide enhanced stability by bonding the first and second sternum portions 12 and 14 in multiple directions.

Figure 16:
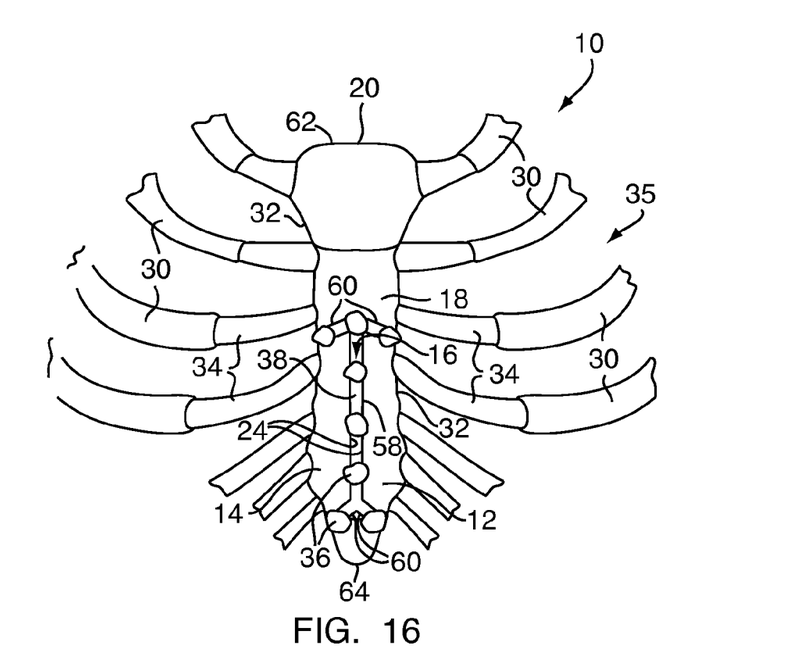
FIG. 16 is a front view of a sternum closed by adhesive after a hemi sternotomy according to another embodiment of the present invention.

Similarly, referring to FIG. 16, the methods of the present invention may also be used to close a sternum 10 after a hemi sternotomy, wherein the incision 16 includes longitudinal portion 58 extending through a central part of the sternum 10 along the midline of the anterior surface 18 with transverse incision portions 60 at the upper and lower ends of the longitudinal portion 58 to separate the sternum 10 into first and second sternum portions 12 and 14, as well as upper and lower sternum portions 62 and 64. During the sternum closure procedure, adhesive 36 may be applied to the incision 16 in the same manner discussed above and is preferably applied to both the transverse portions 60 and the longitudinal portion 58 to provide enhanced stability by bonding the first and second sternum portions 12 and 14 in multiple directions.

An advantage of the methods for sternal closure according to the present invention over the prior art is that the adhesive 36, 136, 236, 336, 436, 636 and 736 resists sliding of one cut surface 24, 424, 524 and 624 relative to the other, flexing motion of the first sternum portion 12, 112, 212 312, 412, 512, 612 and 712 and/or the second sternum portion 14, 114, 214, 314, 414, 514, 614 and 714 about the cut surfaces 24, 424, 524 and 624, as well as relative motion between the first sternum portion 12, 112, 212 312, 412, 512, 612 and 712 and the second sternum portion 14, 114, 214, 314, 414, 514, 614 and 714 in the direction normal to the cut surfaces 24, 424, 524 and 624. Thus, the present invention is able to reduce pain and discomfort experienced by patients due to all of these relative movements. Additionally, the present invention reduces the likelihood of other complications caused by relative motion of the first sternum portion 12, 112, 212 312, 412, 512, 612 and 712 and second sternum portion 14, 114, 214, 314, 414, 514, 614 and 714, such as infections.

The present invention is also advantageous over the prior art because resisting the shearing and flexing relative movement of the first sternum portion 12, 112, 212 312, 412, 512, 612 and 712 and the second sternum portion 14, 114, 214, 314, 414, 514, 614 and 714 reduces the buildup of soft fibrous scar tissue across the incision 16, 116, 216, 516, 616 and 716 at the surgical site, which may result in a non-union or dehiscence. Thus, further surgery to rejoin the first sternum portion 12, 112, 212 312, 412, 512, 612 and 712 and the second sternum portion 14, 114, 214, 314, 414, 514, 614 and 714 may be avoided by the application of adhesive 36, 136, 236, 336, 436 and 736 according to the methods of the present invention.

Additionally, the present invention is advantageous over the prior art plate devices because the cured adhesive 36, 136, 236, 336, 436, 636 and 736 can be cut in a similar manner to bone, i.e. with a sternal saw. Thus, if necessary, the present invention allows for future access to the thoracic cavity to be gained quickly using known techniques.

The present invention is also advantageous in that it can be implemented to resist the shearing and flexing relative movement of the first sternum portion 12, 112, 212 312, 412, 512, 612 and 712 and the second sternum portion 14, 114, 214, 314, 414, 514, 614 and 714 while still being used with additional compressive devices 40, which provide compressive force for resisting separation of the first sternum portion 12, 112, 212 312, 412, 512, 612 and 712 and the second sternum portion 14, 114, 214, 314, 414, 514, 614 and 714 in the direction normal to the cut surfaces 24, 424, 524 and 624. Additionally, when used with compressive devices 40, the adhesive 36, 136, 236, 336, 436, 636 and 736 of the present invention allows for fewer compressive devices 40 to be used when compared to prior art sternal closure devices. Thus, the risk of injury to the patient due to wires or cables being passed behind the sternum 10, 110, 210, 310, 410, 510, 610 and 710 and across surgical grafts is reduced.

Additionally, the present invention is advantageous over the prior art because it provides a method for inhibiting the compressive devices 40 from cutting into the sternum 10, 110, 210, 310, 410, 510, 610 and 710, which can lead to loosening of the compressive devices 40 and separation of the first sternal portion 12, 112, 212 312, 412, 512, 612 and 712 and the second sternum portion 14, 114, 214, 314, 414, 514, 614 and 714 that can result in pain, delayed healing and/or additional surgical procedures.

Although this invention has been shown and described with respect to the detailed embodiments thereof, it will be understood by those skilled in the art that various changes in form and detail thereof may be made without departing from the spirit and the scope of the invention. For example, the geometric features 546 may be formed in a variety of shapes including rectangular and trapezoidal.

What is claimed is:

1. A method for sternal closure comprising:
applying an adhesive to at least a portion of an incision between at least a first sternum portion and at least a second sternum portion; and
maintaining the first sternum portion proximate to the second sternum portion until the adhesive has at least partially bonded with the first sternum portion and the second sternum portion;
wherein the adhesive is applied over the incision at intervals with gaps in between.

2. The method according to claim 1, wherein the adhesive is applied to at least one of a first cut surface of the first sternum portion and a second cut surface of the second sternum portion.

3. The method according to claim 1, wherein the adhesive is a polymeric adhesive.

4. The method according to claim 1, wherein the adhesive is osteoconductive.

5. The method according to claim 1, additionally comprising:
compressing the first sternum portion and the second sternum portion together.

6. The method according to claim 5, wherein compressing the first sternum portion and the second sternum portion includes applying a compression device to at least the first and second sternum portions.

7. The method according to claim 6, wherein the compression device is a wire.

8. The method according to claim 7, additionally comprising:
introducing adhesive to contact regions where the wire contacts the cortical bone of the first and second sternum portions.

9. The method according to claim 5, wherein compressing the first sternum portion and the second sternum portion includes applying cable to at least the first and second sternum portions.

10. The method according to claim 9, additionally comprising:
introducing adhesive to the contact regions where the cable contacts the cortical bone of the first and second sternum portions.

11. The method according to claim 1, additionally comprising:
forming at least one interface feature in the first sternum portion and the second sternum portion.

12. The method according to claim 11, wherein the interface feature extends over a portion of the length of the incision.

13. The method according to claim 11, wherein the interface feature extends over substantially the entire length of the incision.

14. The method according to claim 11, additionally comprising:
inserting a polymeric insert into the interface feature to form a mechanical joint.

15. The method according to claim 14, wherein the polymeric insert has a bowtie shape.

16. The method according to claim 1, additionally comprising:
preparing the incision before applying the adhesive.

17. The method according to claim 16, wherein preparing the incision includes cleaning cut surfaces of the first and second sternum portions.

18. The method according to claim 1, additionally comprising:
spanning the incision with a structural member.

19. The method according to claim 18, additionally comprising:
coating the structural member with adhesive.

20. The method according to claim 18, wherein the structural member is a biscuit.

21. The method according to claim 20, additionally comprising:
pressing the biscuit into cancellous bone of at least one of the first and second sternum portions.

22. The method according to claim 18, additionally comprising:
cutting away a portion of cancellous bone to accommodate the structural member.

23. The method according to claim 22, additionally comprising:
forming the structural member during the surgical procedure.

24. The method according to claim 23, wherein the structural member is made of material substantially similar to the adhesive.

25. A method for sternal closure comprising:
applying an adhesive to at least a portion of an incision between at least a first sternum portion and at least a second sternum portion;
maintaining the first sternum portion proximate to the second sternum portion until the adhesive has at least partially bonded with the first sternum portion and the second sternum portion;
compressing the first sternum portion and the second sternum portion together by applying a wire to at least the first and second sternum portions; and
introducing adhesive to contact regions where the wire contacts the cortical bone of the first and second sternum portions.

26. A method for sternal closure comprising:
applying an adhesive to at least a portion of an incision between at least a first sternum portion and at least a second sternum portion;
maintaining the first sternum portion proximate to the second sternum portion until the adhesive has at least partially bonded with the first sternum portion and the second sternum portion; and
forming at least one interface feature in the first sternum portion and the second sternum portion;
wherein forming the at least one interface feature includes forming a chamfer.

27. A method for sternal closure comprising:
applying an adhesive to a first surface of at least a first sternum portion;
approximating the first sternum portion to at least a second sternum portion; and
maintaining the first sternum portion proximate to the second sternum portion until the adhesive has bonded with the first sternum portion and the second sternum portion;
wherein the adhesive is applied to the first surface at intervals with at least one gap in between.

28. A method for sternal closure comprising:
applying an adhesive to an incision between at least a first sternum portion and at least a second sternum portion; and
compressing the first sternum portion and the second sternum portion until the adhesive has bonded with the first sternum portion and the second sternum portion;
wherein the adhesive is applied to the incision an interval with at least one gap in between.

29. The method according to claim 28, wherein the adhesive is an expandable adhesive, and infiltrates at least a portion of cancellous bone of at least one sternum portion by means of expansion.

30. A method for sternal closure comprising:
physically removing substantially all loose bone fragments and other material from a first cut surface of a first sternum portion and a second cut surface of a second sternum portion to expose cancellous bone within the sternum portions;
applying an adhesive to at least a portion of the first sternum portion at intervals with at least one gap in between;
compressing at least a portion of the first sternum portion to at least a portion of the second sternum portion;
maintaining the compression sufficiently to allow the adhesive to infiltrate at least a portion of the cancellous bone of at least one sternum portion; and
allowing the adhesive to polymerize.

31. A method for sternal closure comprising:
applying an adhesive to a first surface of at least a first sternum portion;
approximating the first sternum portion to at least a second sternum portion; and
allowing the adhesive to expand into cancellous bone of the first sternum portion and the second sternum;
wherein the adhesive is applied to the first surface at intervals with at least one gap in between.

32. A method for sternal closure comprising:
applying an adhesive to at least a portion of an incision between at least a first sternum portion and at least a second sternum portion;
compressing the first sternum portion and the second sternum portion together by applying cable to at least the first and second sternum portions;
introducing adhesive to the contact regions where the cable contacts the cortical bone of the first and second sternum portions; and
maintaining the first sternum portion proximate to the second sternum portion until the adhesive has at least partially bonded with the first sternum portion and the second sternum portion.

* * * * *